United States Patent [19]

Burt et al.

[11] Patent Number: 5,136,075
[45] Date of Patent: * Aug. 4, 1992

[54] PROCESS FOR TRANSHALOGENATING A HALOPHOSPHORUS COMPOUND WITH FLUORIDE

[75] Inventors: Edward A. Burt, Baton Rouge, La.; Lester P. J. Burton, Wilmington, Del.; Meng-Sheng Ao; Barbara C. Stahly, both of Baton Rouge, La.

[73] Assignee: Ethyl Corporation, Richmond, Va.

[*] Notice: The portion of the term of this patent subsequent to Sep. 17, 2008 has been disclaimed.

[21] Appl. No.: 723,594

[22] Filed: Jul. 1, 1991

Related U.S. Application Data

[60] Division of Ser. No. 487,787, Mar. 5, 1990, Pat. No. 5,049,691, which is a continuation-in-part of Ser. No. 239,409, Sep. 1, 1988, abandoned.

[51] Int. Cl.$^5$ .................. C07F 9/6574; C07F 9/14; C07F 9/146
[52] U.S. Cl. .................... 558/84; 558/140
[58] Field of Search .................... 558/84, 140

[56] References Cited

U.S. PATENT DOCUMENTS 5,049,691 9/1991 Burt et al. .................... 558/84

Primary Examiner—Mary C. Lee
Assistant Examiner—Michael G. Ambrose
Attorney, Agent, or Firm—Joseph D. Odenweller; Patricia J. Hogan

[57] ABSTRACT

Phosphorus compounds having at least one chlorine, bromine or iodine bonded directly to phosphorus are transhalogenated with fluorine by reaction with anhydrous hydrogen fluoride in an inert solvent, e.g., xylene, methylene chloride, in a manner such that said anhydrous hydrogen fluoride is added to said phosphorus compound at a rate such that said anhydrous hydrogen fluoride reacts with said phosphorus compound without the accumulation of an amount of unreacted anhydrous hydrogen fluoride which is sufficient to cause substantial decomposition of the desired fluorophosphorus product. A catalytic amount of a pyridine-type compound may optionally included in the reaction.

9 Claims, No Drawings

PROCESS FOR TRANSHALOGENATING A HALOPHOSPHORUS COMPOUND WITH FLUORIDE

This application is a division of application Ser. No. 487,787, filed Mar. 5, 1990, now U.S. Pat. No. 5,049,691, which in turn is a continuation-in-part of Ser. No. 239,409, filed Sep. 1, 1988, abandoned.

BACKGROUND

It is known that fluorine can be exchanged for chlorine, bromine or iodine bonded to phosphorus by reaction of the halophosphorus compound with a metal fluoride. The transhalogenation reaction is quite slow and difficult to push to completion. It is sometimes desirable to replace chlorine, bromine, or iodine bonded to phosphorus with a fluorine atom. For example, L. P. J. Burton U.S. Pat. No. 4,912,155, describes a family of aryl fluorophosphites that are very effective stabilizers in polyolefins, especially in combination with phenolic antioxidants, and are also hydrolytically stable. These compounds are made by first forming an aryl chlorophosphite by reaction of an appropriate aromatic hydroxy compound with $PCl_3$ to form an aryl mono or dichlorophosphite and then transhalogenating the chlorine atom with fluorine by reaction with a metal fluoride such as potassium fluoride.

L. P. J. Burton and M. S. Ao, in U.S. Pat. No. 5,061,818, disclose that the transhalogenation of a chlorine, bromine or iodine atom bonded directly to phosphorus by reaction with a fluoride salt can be sharply promoted by including in the reaction mixture a hydrogen halide salt of a pyridine-type compound.

In U.S. Pat. No. 4,929,745, there is disclosed a method for exchanging a halogen bonded to a phosphorus compound having a halogen selected from chlorine, bromine or iodine bonded directly to phosphorus using a hydrogen fluoride salt of a pyridine-type compound such as pyridine hydrofluoride as the source of the fluorine.

SUMMARY OF THE INVENTION

It has now been discovered that the transhalogenation of phosphorus compounds having at least one chlorine, bromine or iodine bonded directly to phosphorus with fluorine can be achieved in short reaction time (typically within 0.5 to 4 hours) with or without the use of a pyridine-type hydrohalide catalyst and without the use of expensive metal fluoride reactants by reacting said phosphorus compounds with anhydrous hydrogen fluoride in an inert solvent in accordance with the teachings set forth herein. In conducting the process of the present invention, it is essential that hydrogen fluoride is added to the reaction mixture at a rate such that it reacts with the halogen-bound phosphorus compound as it is being introduced into the reaction mixture rather than all at once. This prevents accumulation of a substantial amount of unreacted hydrogen fluoride in the reaction mixture. It has been found that the presence of substantial amounts of unreacted hydrogen fluoride causes decomposition of the desired fluorophosphorus product. Further, it also is essential to the successful practice of the present invention that the anhydrous form of hydrogen fluoride is used in the process rather than aqueous hydrogen fluoride as the use of hydrofluoric acid has been found to result in the formation of unwanted decomposition products which will be discussed more fully below.

DESCRIPTION OF THE PREFERRED EMBODIMENTS

Thus, a preferred embodiment of the invention is a process for exchanging a halogen bonded to a phosphorus atom with fluorine to form a fluorophosphorus product said process comprising adding anhydrous hydrogen fluoride to a phosphorus compound having a halogen selected from chlorine, bromine or iodine bonded directly to phosphorus in an inert solvent at a rate such that said anhydrous hydrogen fluoride reacts with said phosphorus compound without the accumulation of an amount of unreacted anhydrous hydrogen fluoride in the reaction mixture which is sufficient to cause substantial decomposition of the desired fluorophosphorus product.

The phosphorus-bound halogen that is exchanged with fluorine can be chlorine, bromine or iodine. The exchange is more difficult with chlorine but phosphorus-bound chlorine compounds are the most readily available. Accordingly the preferred phosphorus-bound halogen is chlorine.

The process can be conducted in a number of inert solvents. Inert solvents include aliphatic hydrocarbons such as hexane, heptane, octane, cyclohexane, and the like including mixtures thereof.

Useful inert solvents include the aromatic hydrocarbon solvents which boil in the range of about 80°–176° C. These include benzene, toluene, xylene and mesitylene including all isomers and all mixtures thereof.

Halogenated hydrocarbon solvents such as carbon tetrachloride, 1,2-dichloroethane, methylene bromide, methylene chloride, 1,1,2-trichloroethane, chlorobenzene, dichlorobenzene and the like can be used as solvents.

Use of halogenated solvents has a distinct advantage in that the reaction will proceed at a good rate at much lower temperatures compared to a hydrocarbon solvent. Lower temperatures result in a purer product. Although a preferred temperature range for the transhalogenation process is about 40°–200° C., it has been found that with halogenated hydrocarbon solvents the reaction proceeds efficiently at about 40°–80° C. A highly preferred method of conducting the process is in refluxing chlorinated hydrocarbon solvents, more preferably those having a normal boiling point below 80 C, e.g., methylene chloride, 1,1,1-trichloroethane, chloroform, carbon tetrachloride, 1,1-dichloroethane, 1,2-dichloroethane and the like.

The most preferred solvent is methylene chloride and the most preferred reaction condition is in refluxing methylene chloride.

The amount of solvent used should be an amount that will dissolve the reactants. A useful amount is about 50–500 parts by weight solvent per 100 parts of phosphorus compound.

The amount of hydrogen fluoride used in the reaction should be at least a stoichiometric amount. This is 1 equivalent of hydrogen fluoride per equivalent of phosphorus-bound halogen. Amounts less than the stoichiometric amount can be used, however, employment of amounts less than the stoichiometric amount result in depressed yields of the desired halophosphorus product. In general, use of about 1–10 equivalents of hydrogen fluoride per equivalent of phosphorus bound halogen is recommended. More preferably, the amount of hydrogen fluoride is about 1–5 equivalents and most preferably about 1.0–1.4 equivalents per equivalent of phosphorus bound halogen.

As noted previously, applicants have found that the use of hydrogen fluoride in other than in its anhydrous form results in the formation of decomposition products and therefore decreased yields of the desired halophosphorus reaction product. Thus, the use of aqueous hydrogen fluoride (i.e., hydrofluoric acid) as a reactant is to be avoided in the transhalogenation reaction of the present invention.

Further, applicants have also found that it is essential to the successful practice of the present process that anhydrous hydrogen fluoride is deliberately added to the reaction mixture at a rate such that it reacts with the halogen-bound phosphorus compound essentially as it is being introduced into the reaction mixture rather than all at once to prevent the presence of a substantial amount of unreacted hydrogen fluoride in the reaction mixture. It has been found that the accumulation of substantial amounts of unreacted hydrogen fluoride in the reaction mixture can cause complete or nearly complete decomposition of the desired halophosphorus compound to occur. By substantial amounts, applicants mean amounts of unreacted anhydrous hydrogen fluoride sufficient to cause complete or nearly complete decomposition of the desired halophosphorus product. This can readily be determined by one skilled in the art without undue experimentation by sampling the reaction mixture periodically during the course of the reaction and analyzing by gas chromotography for product decomposition as the reaction progresses.

In general, accumulated amounts of unreacted hydrogen fluoride should not exceed about 0.2 mol per mol of phosphorus compound and preferably should be less than 0.1 mol per mol of phosphorus compound and still more preferably should not exceed 0.01 mol per mol of phosphorus compound The presence of excessive anhydrous hydrogen fluoride is readily apparent when the product undergoes substantial decomposition.

At the present time, applicants do not fully understand that mechanism or mechanisms responsible for causing the formation of unwanted decomposition products and decreased yields of halophosphorus product when hydrofluoric acid is used in lieu of anhydrous hydrogen fluoride in the practice of the present process, or the mechanism or mechanisms responsible for causing halophosphorus product degradation when hydrogen fluoride is introduced into the reaction mixture at a rate which produces the accumulation of unreacted hydrogen fluoride in amounts sufficient to cause the halophosphorus reaction product to decompose. Applicants believe, however, that the use of aqueous hydrogen fluoride in the reaction as the fluorinating agent instead of anhydrous hydrogen fluoride causes hydrolysis of the phosphorus-bonds to occur during transhalogenation which results in the formation of unwanted decomposition products instead of the desired fluorophosphorus product. Further, applicants believe that when hydrogen fluoride is fed into the reaction mixture at a rate faster than it can react with the halogen-bound phosphorus starting material, cleavage of the phosphorus bond contained in the fluorophosphorus product occurs causing the desired fluorophosphorus reaction product to decompose into smaller molecules. Knowledge of the mechanisms responsible for the occurrences of these events, however, is not necessary in order to obtain the unexpected benefits of the present invention.

The fluoride exchange reaction proceeds efficiently in the presence of a pyridine-type catalyst although the pyridine-type catalyst is not essential to the success of the transfluorination. Pyridine-type catalysts include organic compounds that include a pyridine ring in their structure such as pyridine, alpha-picoline, beta-picoline, gamma-picoline, quinoline, isoquinoline, 7-methylquinoline, 2,3dimethylaquinoline, lepidine, quinaldine, 2,6-di-tert-butylpyridine, acridine, quinolinic acid, nicotinic acid, 2-aminopyridine, 2-phenylpyridine and the like including mixtures thereof.

Resin-bound pyridine can also be used as the catalyst. An example of such a resin-bound pyridine is described in U.S. Pat. No. 2,739,948. These are vinyl polymer resins that are cross-linked with divinylbenzene, divinylpyridine or other conventional cross-linking agent that renders the polymer insoluble in the reaction mixture. The resin contains pyridyl groups covalently bonded to the polymeric backbone.

When a pyridine-type catalyst is used (which use is not essential) only a catalytic amount is added to the reaction mixture A useful range is about 0.01–0.5 moles of pyridine-type compound per mole of phosphorus compound. A preferred range is about 0.05–0.15 mole of pyridine-type compound per mole of phosphorus compound.

In the most preferred mode of operation, the pyridine catalyst is added to the initial reaction of phenolic compound with phosphorus chloride, bromide or iodide as described in Burton et al., U.S. Pat. No. 5,061,818. For example, the reaction of 100 grams of 2,2'-ethylidenebis (4,6-di-tert-butylphenol) with 37.6 grams of $PCl_3$ in 130 grams of xylene containing 10 grams of pyridine catalyst forms 2,2'-ethylidenebis(4,6-di-tert-butylphenyl) chlorophosphite in high yield. In the preferred mode of practicing the present process, the pyridine hydrochloride formed in that reaction is left in the reaction mixture as anhydrous HF is added to cause the transfluorination. As explained previously, it is not necessary to have the pyridine-type hydrohalide salt in the reaction mixture since the transfluorination will proceed in its absence.

The transhalogenation should be conducted at a temperature high enough to cause the halogen exchange to proceed but not so high as to cause undesired degradation of the reaction products. A useful temperature range is about 20°–300° C., more preferably about 40°–200° C. and most preferably at the atmospheric pressure reflux temperature of the reaction mixture. Higher temperatures will of course require a sealed system under pressure.

The reaction time should be long enough to complete the reaction. The reaction is generally complete in 0.5–4 hours and in most cases in approximately 1.0–2.0 hours.

The phosphorus compounds having chlorine, bromine or iodine bonded to phosphorus can have one or two of such halogens bonded to phosphorus. The remaining group or groups bonded to phosphorus are substituted or unsubstituted hydrocarbyl, hydrocarbyloxy or hydrocarbylthio groups. Examples of such halo phosphorus compounds are methyl dichlorophosphite, ethyl dichlorophosphite, butyl dichlorophosphite, dodecyl dichlorothiophosphite, eicosyl dichlorophosphite, triacontyl dichlorophosphite, methyl dibromophosphite, propyl dibromophosphite, tetradecyl diiodophosphite, eicosyl chlorobromophosphite, triacontyl bromoiodophosphite, methyl dichlorophosphate, O-ethyl dichlorothiophosphate, decyl dichlorophosphate, eicosyl dichlorophosphate, O-triacontyl dichlorothiophosphate, methyl dibromophosphate, octyl dibromophosphate, octadecyl dibromothiophosphate, triacontyl dibromophosphate, methyl diiodophosphate, hexadecyl diiodophosphate, eicosyl chloroiodophosphate, O-methyl dichlorothiophosphate, O-decyl dibromothiophosphate, eicosyl diiododithiophosphite, triacontyl dichlorothiophosphonate, phenyl dichlorophosphite, phenyl dibromophosphite, phenyl diiodophosphite, benzyl dichlorophosphite, benzyl dibromophosphite, methyldichlorophosphine, butyldichlorophosphine, dodecyldichlorophosphine, eicosyldibromophosphine, triacontyldiiodophosphine, cyclohexyl dichlorophosphite, cyclohexyl dibromophosphite, cyclohexyl dichlorothiophosphite, cyclohexyl dibromodithiophosphate, dimethyl chlorophosphite, didodecyl chlorophosphite, dieicosyl bromophosphite, ditriacontyl iodophosphite, dimethylchlorophosphine, didodecylbromophosphine, dimethyl chlorothiophosphite, dieicosyl bromodithiophosphate, dimethyl chlorophosphate, didodecyl bromophosphate, dieicosyl bromophosphate, diphenyl chlorophosphite, diphenyl bromophosphite, diphenyl chlorophosphate, diphenyl bromotrithiophosphate, diphenyl chlorophosphate, dibenzyl chlorophosphate, dibenzyl bromophosphite, diphenyl chlorotrithiophosphate, dicyclohexyl chlorophosphate, phenyldichlorophosphine, diphenylbromophosphine, dibenzylchlorophosphine, dimethylchlorophosphine, didodecylbromophosphine, methyleicosyliodophosphine, benzyldibromophosphine and the like.

The preferred phosphorus compounds have the structure

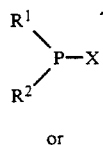

or

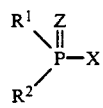

wherein X is chlorine, bromine or iodine, Z is oxygen or sulphur, $R^1$ is selected from the group consisting of substituted and unsubstituted alkoxy, thioalkoxy, aryloxy, thioaryloxy, cycloalkoxy, alkenoxy, and arylalkoxy and $R^2$ is selected from the same group as $R^1$ or is X or $R^1$ and $R^2$ can jointly form a substituted or unsubstituted divalent hydrocarbon group bonded at each end through oxygen or sulphur to the phosphorus atom in structure I or II. More preferably $R^2$ is not X.

Examples of the preferred starting phosphorus compounds are dimethyl chlorophosphite, diethyl chlorophosphite, diethyl bromophosphite, dibutyl iodophosphite, dioctyl chlorophosphite, didodecyl bromophosphite, dieicosyl iodophosphite, triacontyl dichlorophosphite, butyl dibromophosphite, methyl dodecyl chlorophosphite, eicosyl dichlorophosphite, triacontyl dibromophosphite, dimethyl chlorothiophosphite, dodecyl dibromothiophosphite, dioctadecyl chlorothiophosphite, phenyl dichlorophosphite, diphenyl bromophosphite, di(4-tert-butylphenyl) chlorophosphite, di(2,4- di-tert-butylphenyl) bromophosphite, 2-isopropyl-4-methylphenyl dichlorophosphite, di(4-tert-hexylphenyl) chlorophospite, diphenyl chlorothiophosphite, phenyl dibromothiophosphite, 1-naphthyl dichlorophosphite, dicyclohexyl chlorophosphite, dicyclooctyl bromophosphite, cyclododecyl dichlorophosphite, dicyclohexyl bromothiophosphite, diallyl iodophosphite, di-(but-2-enyl) chlorophosphite, benzyl dichlorophosphite, dibenzyl bromophosphite, di(alpha-methylbenzyl) chlorophosphite, ethyleneglycol chlorophosphite, 2,2'-methylenebis(4,6-di-tert-butylphenyl) chlorophosphite, 2,2'-methylenebis(4-methyl-6-tert-butylphenyl) bromophosphite, 2,2'-bis(4,6-di-tert-butylphenyl) chlorophosphite, 2,2'-bis(4,6-di-tert-butylphenyl) chlorophosphate, 2,2'-ethylidenebis(4,6-di-tert-butylphenyl) chlorophosphite, 2,2'-ethylidenebis(4,6-di-tert-butylphenyl) chlorophosphate, di(2,4-di-tert-butylphenyl) chlorophosphate, di(2,6-di-tertbutylphenyl) chlorophosphite, 2,4-di-tert-butylphenyl dichlorodithiophosphate, di[4-(octadecyloxycarbonylethyl)-2,6-tertbutylphenyl] chlorophosphite and the like.

In the more preferred phosphorus compounds $R^1$ and $R^2$ jointly form a divalent hydrocarbon group having the structure

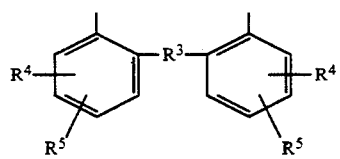

wherein $R^3$ is a methylene or alkylidene bridge or is absent forming a direct ortho-ortho bond between the benzene rings, $R^4$ and $R^5$ are independently selected from alkyl groups, cycloalkyl groups and aralkyl groups and the unsubstituted bond on each benzene ring is bonded through oxygen to said phosphorus atom in structures I or II.

Examples of phosphorus compounds which contain the above divalent hydrocarbon group are 2,2'-methylenebis(4-methyl-6-tertbutylphenyl) chlorophosphite, 2,2'-methylenebis(4-methyl-6-tertbutylphenyl) chlorophosphate, 2,2'-methylenebis(4,6-di-tert-butylphenyl) bromophosphite, 2,2'-ethylidenebis(4-methyl-6-tert-butylphenyl) chlorophosphite, 2,2'-ethylidenebis(4-methyl-6-tert-butylphenyl) chlorophosphate, 2,2'-isopropylidenebis(4-methyl-6-tertpentylphenyl) bromophosphite, 2,2'-butylidenebis(4,6-di-tert-butylphenyl) chlorophosphite, 2,2'-bis(4-sec-dodecyl-6-tert-butylphenyl) chlorophosphate, 2,2'-bis(4-methyl-6-tert-hexylphenyl) bromophosphite, 2,2'-bis(4-methyl-6-cyclohexylphenyl) chlorophosphate, 2,2'-ethylidenebis(4,6-dicyclohexylphenyl) chlorophosphite, 2,2'-methylenebis[4,6-di(alpha-methylbenzyl)phenyl] bromothiophosphite, 2,2'-ethylidenebis(4-methyl-6(alpha-methylbenzyl)phenyl) chlorophosphite, 2,2'-bis[4,6-di(alpha-methylbenzyl)phenyl] bromophosphite and the like.

In a highly preferred embodiment the $R^4$ groups are bonded at the 6,6'-positions and the $R^5$ groups are bonded at the 4,4'-positions in structure III. Still more preferably both $R^4$ groups are tert-alkyls having 4-12 carbon atoms and $R^5$ is $C_1$ alkyl, especially a tert-alkyl of 4-12 carbon atoms.

The most preferred phosphorus compound used as a starting material is 2,2'-ethylidenebis(4,6-di-tert-butylphenyl) chlorophosphite.

The reaction is readily carried out by placing the phosphorus compound and a solvent in a stirred reaction vessel, heating to reaction temperature and adding anhydrous hydrogen fluoride to the vessel The hydrogen fluoride is added by any convenient method. For example, it can be purged through the system or bubbled into the liquid phase using a "dip-leg". It can be added either as a liquid or a gas. Alternatively, the phosphorus compound can be exposed to hydrogen fluoride under pressure where pressures can range from about 5–100 psig, or higher.

The product can be recovered by conventional means such as crystallization or distillation.

The following examples show how the reaction is conducted.

EXAMPLE 1

The 2,2'-ethylidenebis(4,6-di-tert-butylphenyl) chlorophosphite starting material was made by placing 400 grams 2,2'-ethylidenebis(4,6-di-tert-butylphenol), 11.0 grams of a poly-4-vinylpyridine cross-linked resin catalyst obtained from the Reilly Tar and Chemical Corp. identified as Reillex TM 425 polymer and 750 grams of xylene in a reaction vessel. The cross-linked vinyl polymeric resin had previously been dried is a vacuum oven at 125° C. overnight. The mixture was stirred and heated under nitrogen to 130° C. At 130° C., 150 grams of PCl$_3$ was fed to the reaction mixture incrementally over a period of 4 hours while maintaining a nitrogen sweep over the reaction mixture to assist in HCl removal. At the end of 4 hours, an additional 10 grams of PCl$_3$ was added to the reaction mixture and the reaction was continued for another 4 hours. The liquid phase was then decanted from the Reillex TM 425 polymer. This method of preparation is described in U.S. Pat. No. 4,894,481 entitled "Method of Making Cyclic Aryl Chlorophosphites." Gas chromatography (GC) analysis showed the reaction product excluding solvent, PCl$_3$ and resin catalyst to be 96.8 area percent 2,2'-ethylidenebis(4,6-di-tert-butylphenyl) chlorophosphite and 3.2 area percent 2,2'-ethylidenebis(4,6-di- tert-butylphenyl) hydrogenphosphonate.

To 342 grams of the above decanted- liquid phase in a 600 mL Monel Parr autoclave, there was added slowly 5.7 grams of gaseous anhydrous hydrogen fluoride over a 2.5 hour period with stirring while maintaining the reaction temperature at approximately 95° C. A low nitrogen sweep was maintained through the reaction vessel during the last 30 minutes of the reaction to assist in HCl removal. The temperature was allowed to drop to 90° C. and xylene was vacuum stripped from the reaction mixture. Isopropanol (116 grams) was added to the reactor and the temperature dropped to 85° C. where it was maintained for 30 minutes. The mixture was cooled to 5° C. over a period of 1 hour. The resultant solid precipitate was recovered by filtration. The filter cake was washed with 50 grams of isopropanol and dried at 80° C. under vacuum overnight. A total of 92.5 grams, 80% yield based on initial 2,2'-ethylidenebis(4,6-di-ert-butylphenol), of 2,2'-ethylidenebis(4,6-di-tert-butylphenyl) fluorophosphite was obtained.

EXAMPLE 2

This example shows the effect of substituting aqueous hydrogen fluoride in the process of the present invention for anhydrous hydrogen fluoride.

The 2,2'-ethylidenebis(4,6-di-tert-butylphenyl) chlorophosphite starting material was made by heating a mixture of 400 grams of 2,2'ethylidenebis(4,6-di-tert-butylphenol) and 740 grams of xylene in a 2-liter glass round-bottomed flask to 80° C. and thereafter adding 4.grams of pyridine to the reaction mixture. The mixture was then heated to reflux (130° C.) and 150 grams of PCl$_3$ was fed to the reaction mixture over a 1 hour period of time. Gas chromatography (GC) analysis showed the reaction product excluding solvent, PCl$_3$ and pyridine hydrochloride to be 96.5 area percent 2,2'-ethylidenebis(4,6-di-tert-butylphenyl) chlorophosphite, 1.8 percent 2,2'-ethylidenibis(4,6-di-tert-butylphenyl) hydrogenphosphonate and 0.2 percent, 2,2'-ethylidenebis(4,6-di-tert-butylphenol).

To 400 grams of this reaction mixture placed in a 600 mL Monel Parr autoclave, there was added slowly 11.3 grams of aqueous hydrogen fluoride (48 wt. % HF) with stirring. The resultant solution was heated to 80° C. over a period of 2 hours and was maintained at this temperature for another 1 hour. GC analysis after 1 hour of reaction gave 96 area percent 2,2'-ethylidenebis(4,6-di-tert-butylphenyl) chlorophosphite (essentially no reaction). GC after 2 hours from start of reaction gave 21 area percent 2,2'-ethylidenebis(4,6-di-tert-butylphenyl) chlorophosphite, 39.8 area percent 2,2'-ethylidenebis(4,6-di-tertbutylphenyl) hydrogenphosphonate, 2.1 area percent 2,2'-ethylidenebis(4,6-di-tert-butylphenol) and only 37.0 area percent 2,2'ethylidenebis(4,6-di-tert-butylphenyl) fluorophosphite.

EXAMPLE 3

This example shows the degradation effect of adding an excessive amount of anhydrous hydrogen fluoride reactant to the reaction mixture.

The 2,2'-ethylidenebis(4,6-di-tert-butylphenyl) chlorophosphite starting material was made by placing 150 milliliters of toluene into a 50 milliliter 4-necked round bottom flask equipped with two addition funnels, a thermometer and an overhead stirrer under nitrogen. A solution of 10 milliliters of PCl$_3$ in 50 milliliters of toluene was added dropwise to the flask over a 40 minute period while a solution of 47.8 grams of 2,2'-ethylidenebis(4,6-di-tert-butylphenol) in 32 milliliters of triethylamine and 50 milliliters of toluene were added concurrently to the flask dropwise over a 55 minute period of time. After 1.5 hours, the slurry was heated to 40° C. and maintained at this temperature for 1 hour. It was then allowed to cool to ambient temperature and stored overnight. The crude reaction mixture was then filtered and the filtrate concentrated under vacuum to 35 grams of off-white solids. A 32 gram portion of the solids was dissolved in approximately 500 milliliters of n-heptane under nitrogen. The solution was filtered hot, the filtrate concentrated under vacuum to 250 milliliters and allowed to cool to room temperature. The solids were collected. Phosphorus NMR analysis revealed 67 area percent 2,2'-ethylidenebis(4,6-di-tert- butylphenyl) chlorophosphite, 23 percent 2,2'-ethylidenebis(4,6-di-tert-butylphenyl) hydrogenphosphonate and 8.0 percent unknown impurities.

A 1.15 gram portion of this product was combined with 20 milliliters of toluene in a polyethylene bottle under an atmosphere of nitrogen. The reaction vessel was cooled to 10° C. in an ice bath. A 2 to 3 milliliter portion of anhydrous hydrogen fluoride was added to the mixture. The container was closed and stirred for 15 minutes. The bottle was then vented and allowed to warm under a stream of nitrogen to ambient temperature. After 1 hour, nitrogen was bubbled through the solution to remove residual hydrogen fluoride. Analysis by phosphorus NMR of the crude reaction mixture revealed an absence of 2,2'-ethylidenebis(4,6-di-tert-butylphenyl) fluorophosphite as well as 2,2'-ethylidenebis(4,6-di-tert-butylphenyl) chlorophosphite. Gas chromatography revealed several peaks with shorter retention times relative to the chlorophosphite and fluorophosphite compounds.

EXAMPLE 4

This example shows the process conducted in a halogenated hydrocarbon solvent.

To a dried reaction vessel, equipped with a condenser, was charged 800 g methylene chloride, 500 g 2,2'-ethylidene-(4,6-di-tert-butylphenol) (I), 10.1 g pyridine and 170.1 g $PCl_3$ The stirred reaction mass was heated to 46° C. and maintained at reflux until all of ethylidene bisphenol I was reacted. This required 10.3 hours. The resulting suspension was diluted with 1715 g methylene chloride. The reaction mass was heated to reflux and gaseous HF was introduced below the surface. After two hours, 320 g methylene chloride was added and the hydrogen fluoride feed was continued until analysis by gas chromatography showed the reaction to be completed to form 2,2'-ethylidenebis(4,6-di-tert-butylphenyl) fluorophosphite. Next, ammonia gas was passed through the reaction mixture for one hour and the resulting ammonium halide salts were filtered off. The resulting filtrate was fed to a glass reactor containing 1250 g isopropanol heated to 71° C. Methylene chloride was distilled off. The feed time was 1.5 hour. After completion of the feed, 100 g of isopropanol was added and the mixture was heated to 80° C. to complete the removal of methylene chloride. The resulting slurry was cooled to 35° C., filtered and washed with isopropanol. After drying 470 g (85% yield) of white crystalline product was obtained. Analysis by gas chromatography showed the product to contain 97.8% of 2,2'-ethylidenebis(4,6-di-tert-butylphenyl) fluorophosphite.

EXAMPLE 5

To a reaction vessel equipped with a turbine agitator and a reflux condenser was charged 375 g of methylene chloride, 250 g 2,2'-ethylidenebis(4,6-di-tert-butylphenol), 5 g pyridine and 83 g $PCl_3$. The stirred solution was heated to reflux (45° C.) and held at reflux for 22 hours. Byproduct HCl was vented to a scrubber. About 350 g of additional methylene chloride was added during the reaction to replace that lost through the vent and further dilute the reaction. GC analysis showed conversion of the above ethylidenebisphenol to 2,2'-ethylidenebis(4,6-di-tert-butylphenyl) chlorophosphite. While still at reflux, 13.1 g of anhydrous gaseous HF was fed to the reaction mixture through a dip leg. HF feed required 10½ hours. Byproduct HCl was vented to a scrubber. GC analysis showed conversion of the above chlorophosphite to the corresponding fluorophosphite to be complete. Gaseous ammonia was immediately fed to the reaction to neutralize the mixture. The reaction mass was filtered to remove ammonium chloride. The filtrate was heated to distill out methylene chloride which was replaced by adding isopropanol. The temperature reached 81° C. at the end of the methylene chloride removal. The mixture was cooled to 30° C. giving a 50 weight percent solids slurry in isopropanol. The solids were removed and the wet cake was washed with isopropanol and dried under vacuum yield 223 g (80.5 percent yield) of 2,2'-ethylidenebis(4,6-di-tert-butylphenyl) fluorophosphite.

EXAMPLE 6

To a reaction vessel was charged 7618 g methylene chloride and 500 g 2,2'-ethylidenebis(4,6-di-tert-butylphenol) (I). After distilling off 45 g of methylene chloride, 39.4 g of heptane, 10.2 g of pyridine and 171 g of $PCl_3$ were added to the reaction vessel. The stirred reaction mass was heated to 46° C. and refluxed for 5.5 hours. After adding 110 g methylene chloride the reflux was continued for 8 hours. Then 2g $PCl_3$ was added and the reflux was continued for another 5.5 hours. Analysis showed that less than 1% of unreacted ethylidenebisphenol I was present and the rest converted to 2,2'-ethylidenebis(4,6-di-tert-butylphenyl) chlorophosphite. After diluting the slurry with 1300 g of methylene chloride, gaseous HF was introduced to the refluxing mixture. The HF feed was continued until about 99% of the chlorophosphite intermediate had reacted. Next, gaseous ammonia was passed through the mixture for one hour and the resulting ammonium halide salts were filtered off, giving 2140 g of clear filtrate, which contained the fluorophosphite product (GC and P-31 NMR analysis).

To 780 g of heptane heated to 65° C. was added 845 g of the above filtrate in 85 minutes During the addition methylene chloride was distilled off. The distillation was completed by heating the reaction mass to 100° C. After cooling to 5° C. the mixture was filtered and the cake was washed with 250 g cold heptane. After drying 132 g of white crystalline powder was obtained. This represents 60% yield based on starting I. Analysis by GC showed that the product contained 94.4% 2,2'-ethylidenebis(4,6-di-tert-butylphenyl) fluorophosphite.

EXAMPLE 7

A reactor was charged with 1175 g methylene chloride and 782 g 2,2'-ethylidenebis(4,6-di-tert-butylphenol) (I). After distilling off 100 g methylene chloride to dry the system, 15.8 g heated at reflux for 10.5 hours. During the next three hours 15 g $PCl_3$, 2 g pyridine and 300 g methylene chloride were added. After refluxing for another 9.5 hours, analysis showed that all bisphenol I had reacted to form 2,2'-ethylidenebis(4,6-di-tertbutylphenyl) chlorophosphite. Next, gaseous HF was fed to the refluxing reaction mass until GC analysis showed transhalogenation to be complete This required 9.5 hours. After adding 250 g methylene chloride, the reactor was pressured to 3 psig with gaseous ammonia and stirred for one hour. The ammonium salts were filtered off and the filtrate was transferred to a vessel equipped with a distillation head. While distilling off methylene chloride, 1812 g of isopropanol was added at a rate approximately equal to the distillate collection rate. The distillation was stopped when the pot temperature reached 81° C. After cooling to 35° C. the slurry was filtered and the collected solids, after washing with isopropanol, were dried in a vacuum oven. The dried solid weighed 710 g (82% yield) and was shown by GC analysis to contain 97.3% of 2,2'-ethylidenebis(4,6-di-tert-butylphenyl) fluorophosphite.

EXAMPLE 8

To 250 g of methylene chloride in a reaction vessel was added 100 g 2,2'-ethylidenebis(4,6-di-tert-butylphenol) and 2 g of pyridine. After distilling off about 30 g of methylene chloride, 34 g of $PCl_3$ was added and the mixture was stirred at reflux for 10 hours. Analysis by GC showed that all of the bisphenol had reacted to form 2,2'-ethylidenebis(4,6-di-tert-butylphenyl) chlorophosphite. The resulting slurry was diluted with methylene chloride and brought to reflux. Next, HF gas was passed slowly into the slurry until all of the chlorophosphite intermediate had reacted (GC analysis). This required 8.5 hours. The flask was then pressured to 3 psig with ammonia and stirred for 30 minutes. The ammonium salts were filtered off and the filtrate was slowly added to 180 g isopropanol heated to 65° C. Methylene chloride was distilled off during the addition and the distillation was stopped when the pot temperature reached 80° C. The resulting slurry was cooled to ambient temperature, filtered, and the solid cake was washed with isopropanol. After drying 98 g (88% yield) of white crystalline powder was obtained. Analysis by GC and P-31 NMR showed that the product was 96.7% pure 2,2'-ethylidenebis(4,6-di-tert-butylphenyl) fluorophosphite.

EXAMPLE 9

To a reaction vessel was added 600 g methylene chloride, 200 g 2,2'-ethylidenebis(4,6-di-tert-butylphenol), 4 g pyridine and 64.4 g $PCl_3$. The mixture was stirred at reflux (45° C.) for hours. At this point 8.2% of the bisphenol charged was still unreacted. After adding 2.5 g $PCl_3$ the reaction was continued for one hour. Then another portion of $PCl_3$ (1.9 g) was added and the reaction was completed after one hour at 45° C. (An undetermined quantity of $PCl_3$ was found in a cold trap connected to the reflux condenser). The resulting light slurry was maintained at reflux while HF gas was passed slowly into the reaction flask until all of the chlorophosphite intermediate was converted. This required 7 hours. The flask was then pressured with ammonia to 3 psig. After 30 minutes the flask was vented and the reaction mixture was filtered. The product was isolated using the procedure of Example 8. This gave 202 g (91% yield) of product which was shown by GC and P-31 NMR to be 97.1% pure 2,2'-ethylidenebis(4,6-di-tert-butylphenyl) fluorophosphite.

We claim:

1. A process which comprises adding anhydrous hydrogen fluoride to a phosphorus compound having 1–2 halogen atoms selected from chlorine, bromine, or iodine bonded directly to phosphorus at a rate such that the anhydrous hydrogen fluoride reacts with the phosphorus compound to replace said halogen atoms with fluorine atoms and thereby form a fluorophosphorus product without the accumulation of sufficient anhydrous hydrogenfluoride to cause substantial decomposition of the fluorophosphorus product; said process being conducted in an inert solvent and in the presence of a pyridine-type compound or hydrogen halide salt thereof.

2. A process of claim 1 conducted in a halohydrocarbon solvent.

3. A process of claim 2 wherein said halohydrocarbon is methylene chloride and the halogen exchange reaction is carried out at reflux.

4. A process of claim 3 wherein said phosphorus compound has the structure

or

wherein X is chlorine, bromine or iodine, Z is oxygen or sulfur, $R^1$ is selected from the group consisting of substituted and unsubstituted alkoxy, thioalkoxy, aryloxy, thioaryloxy, cycloalkoxy, alkenoxy, and arylalkoxy and $R^2$ is selected from the same group as $R^1$ or is X, or $R^1$ and $R^2$ can jointly form a divalent hydrocarbon group bonded at each end through oxygen or sulfur to the phosphorus atom in structures I or II.

5. A process of claim 4 wherein $R^1$ and $R^2$ jointly form a divalent group having the structure

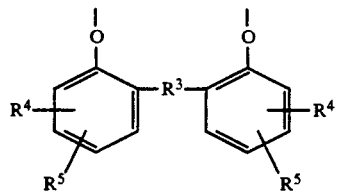

wherein $R^3$ is methylene or alkylidene bridge or forms a direct ortho-ortho bond between the benzene rings, $R^4$ and $R^5$ are independently selected from alkyl groups, cycloalkyl groups and aralkyl groups and the oxygen to said phosphorus atom in structures I or II.

6. A process of claim 5 wherein said divalent group has the structure
wherein $R^4$ and $R^5$ are alkyl group.

7. A process of claim 6 wherein said phosphorus compound has structure I and X is chlorine.

8. A process of claim 7 wherein $R^3$ is present and is the ethylidene group.

9. A process of claim 8 wherein $R^4$ and $R^5$ are tert-butyl groups.

* * * * *